United States Patent
Francis et al.

(10) Patent No.: US 10,791,951 B2
(45) Date of Patent: Oct. 6, 2020

(54) IMAGE DISPLAY INTERFACES

(71) Applicant: Imperial Innovations Limited, London, Greater London (GB)

(72) Inventors: Darrel Francis, Harrow (GB); Prapa Kanagaratnam, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 1209 days.

(21) Appl. No.: 14/785,817

(22) PCT Filed: Apr. 22, 2014

(86) PCT No.: PCT/GB2014/051248
§ 371 (c)(1),
(2) Date: Oct. 20, 2015

(87) PCT Pub. No.: WO2014/174274
PCT Pub. Date: Oct. 30, 2014

(65) Prior Publication Data
US 2016/0073913 A1    Mar. 17, 2016

(30) Foreign Application Priority Data
Apr. 22, 2013    (GB) .................................. 1307211.1

(51) Int. Cl.
*A61B 5/044* (2006.01)
*A61B 5/00* (2006.01)
(Continued)

(52) U.S. Cl.
CPC ............ *A61B 5/044* (2013.01); *A61B 5/0044* (2013.01); *A61B 5/046* (2013.01);
(Continued)

(58) Field of Classification Search
CPC ... A61B 5/044; A61B 5/0044; A61B 5/04011; A61B 5/04012; A61B 5/0422; A61B 5/046; A61B 5/6858; A61B 5/743
See application file for complete search history.

(56) References Cited

U.S. PATENT DOCUMENTS 6,301,496 B1 * 10/2001 Reisfeld ............ A61B 5/04011
345/419
2003/0023130 A1    1/2003 Ciaccio
(Continued)

FOREIGN PATENT DOCUMENTS

EP    1070480    1/2001
WO   199520420    8/1995
(Continued)

OTHER PUBLICATIONS

Kanagaratnam et al., "Relationship Between Connexins and Atrial Activation During Human Atrial Fibrillation", J Cardiovasc Electrophysiol. Feb. 2004: 15(2):206-16.
(Continued)

*Primary Examiner* — Paula J Stice
(74) *Attorney, Agent, or Firm* — Wegman Hessler (57) ABSTRACT

Apparatus for monitoring activation in a heart comprises a probe (100), a plurality of electrodes (101, 102) supported on the probe and each arranged to detect electrical potential at a respective position in the heart during a series of activations, and processing means (104) arranged to analyse the detected electrical potentials to identify a propagation direction of the activation, and to generate an output indicative of that direction.

15 Claims, 7 Drawing Sheets

(51) Int. Cl.
  *A61B 5/042* (2006.01)
  *A61B 5/04* (2006.01)
  *A61B 5/046* (2006.01)
  *A61B 5/06* (2006.01)

(52) U.S. Cl.
  CPC ...... *A61B 5/04011* (2013.01); *A61B 5/04012* (2013.01); *A61B 5/0422* (2013.01); *A61B 5/068* (2013.01); *A61B 5/6858* (2013.01); *A61B 5/743* (2013.01)

(56) References Cited

U.S. PATENT DOCUMENTS

| | | | | |
|---|---|---|---|---|
| 2005/0288599 | A1* | 12/2005 | MacAdam | ............ A61B 5/046 600/509 |
| 2006/0069322 | A1* | 3/2006 | Zhang | ............... A61B 5/04011 600/512 |
| 2012/0089038 | A1 | 4/2012 | Ryu | |
| 2014/0336518 | A1 | 11/2014 | Shuros | |
| 2014/0343388 | A1 | 11/2014 | Thakur | |
| 2014/0343442 | A1 | 11/2014 | Thakur | |
| 2014/0371609 | A1 | 12/2014 | Narayan | |

FOREIGN PATENT DOCUMENTS

| | | |
|---|---|---|
| WO | 2008135731 | 11/2008 |
| WO | WO 2008135731 A1 | 11/2008 |
| WO | 2012092016 | 7/2012 |
| WO | WO 2012092016 A1 | 7/2012 |
| WO | 2014174274 | 10/2014 |
| WO | 2017041891 | 3/2017 |

OTHER PUBLICATIONS

Search Report issued in related Application No. GB1706561.6 dated Sep. 29, 2017; 6 pages.
International Search Report and Written Opinion issued for International Application No. PCT/GB2018/051078 dated Jun. 25, 2018; 13 pages.
Circulation, Kadish, et al., "Vector mapping of myocardial activation", Sep. 1986, p. 603-615, vol. 74, No. 3, Dallas, Texas.
Circulation, Allan C. Skanes, et al., "Spatiotemporal Periodicity During Atrial Fibrillation in the Isolated Sheep Heart", American Heart Association, 1998; pp. 1236-1248; No. 98, Dallas, Texas.
Kanagaratnam et al., "Relationship Between Connexins and Atrial Activation During Human Atrial Fibrillation", Journal of Cardiovascular Electrophysiology, Feb. 2004, 15(2):206-16.
International Preliminary Report on Patentability dated Nov. 5, 2015 for PCT/GB2014/051248 filed Apr. 22, 2014.
Skanes et al., Spatiotemporal Periodicity During Atrial Fibrillation in the Isolated Sheep Heart, Circulation 1998; 98:1236-48.
Narayan et al., "MD Treatment of Atrial Fibrillation by the Ablation of Localized Sources", CONFIRM (Conventional Ablation for Atrial Fibrillation With or Without Focal Impulse and Rotor Modulation) Trial., J Am Coll Cardiol 2012; 60:628-36.
International Search Report dated Sep. 2, 2014 for PCT/GB2014/051248 filed Apr. 22, 2014.

* cited by examiner

Fig. 11

IMAGE DISPLAY INTERFACES

CROSS-REFERENCE TO RELATED APPLICATIONS

This application claims the priority filing benefit of International PCT Application PCT/GB2014/051248 filed Apr. 22, 2014 and published under PCT 21(2) in the English language, Great Britain Patent Application Serial No. 1307211.1 filed Apr. 22, 2013. Each of the above listed applications is incorporated herein by reference.

FIELD OF THE INVENTION

The present invention relates to the detection and pictorial representation of cardiac activation, and in particular of the progression of activation through the heart. It has application in locating sites suitable for ablation therapy, for example to cure atrial fibrillation.

BACKGROUND TO THE INVENTION

Irregular heart beat (arrhythmia) is commonly treated with ablation therapy in a cardiac catheter laboratory. A method is needed to identify where the ablation therapy should be delivered, in order to cure the arrhythmia without having to ablate an unnecessarily large amount of the heart.

Parts of the heart become electrically activated in sequence. In health, this is an orderly and normal sequence, proceeding from the sinus node, through regions of the atrium in a stereotyped pattern. In this type of activation each point on the heart has a well defined propagation direction in which the activation progresses as it passes that point. In arrhythmias, the sequence is not normal. The abnormal sequences may be of two categories: those that show a surface ECG pattern that is obviously regular and repetitive, or those that appear to be irregular and do not show a simple repeating pattern.

Fibrillatory electrical activation of the myocardium is one of the most common causes of cardiac morbidity and mortality. It can affect either the atrium (atrial fibrillation) or the ventricle (ventricular fibrillation). Mathematical modelling and in-vitro studies have suggested that fibrillatory electrical activation can often be driven by electrical rotors (Skanes A C, Mandapati R, Berenfeld O, Davidenko J M, Jalife J. Spatiotemporal periodicity during atrial fibrillation in the isolated sheep heart. Circulation 1998; 98:1236-48) and that a small number, for example one to three, of such rotors may be sufficient to maintain fibrillation in the human heart. If the origin of these rotors can be identified and targeted for treatment, then it may be possible to prevent the death and suffering caused by fibrillatory electrical activation.

Atrial activation during human atrial fibrillation is not identical between different patients. It can be anywhere on a spectrum between completely organised to highly disorganised activation (Kanagaratnam P, Cherian A, Stanbridge R D, Glenville B, Severs N J, Peters N S Relationship between connexins and atrial activation during human atrial fibrillation. J Cardiovasc Electrophysiol. 2004 February; 15(2):206-16). The current state of the art is that, using multi-electrode catheters, it is possible to map the activation sequences using isochronal mapping, ie mapping of the timing of activation over the cardiac surface with points which activate at the same time being identified, eg by the same colour. However this is time-consuming and needs careful expert assessment of each electrogram and comparing it to neighbouring electrograms in order to identify the local activation time and produce an isochronal map. Despite the use of isochronal mapping for human atrial fibrillation using epicardial multi-electrodes catheters for many years, there is no method for identifying rotors that can be implemented to operate satisfactorily in independent hands.

There are several possible explanations for this. First, most techniques have not been able to map the whole chamber with sufficient resolution. Second, it has been assumed that complete rotors will be visible continuously over many seconds or minutes, and remain in the same location. Unlike the mathematical models, human myocardial activation near the refractory period results in wave breakage that distorts the appearance of potential rotors. This makes them hard to locate.

Figure 1:
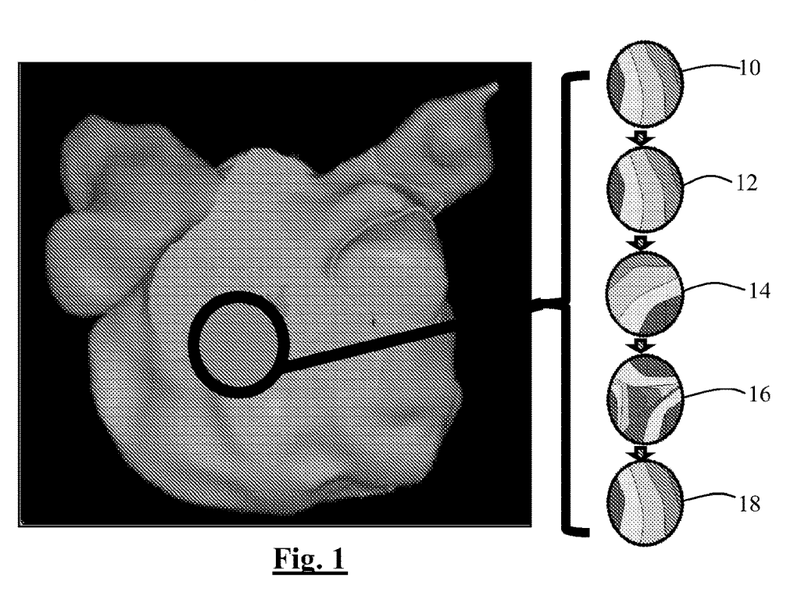
FIG. 1 is a schematic view of a known system for indicating activation propagation direction.

FIG. 1 illustrates the current state of the art using current isochronal mapping methods. A multi-electrode catheter is placed at a location on the endocardium, and is used to map sequential time-windows using the isochronal activation method. Each small circle in the inset is a colour-coded time map of one passage of a wave over that region of the heart, or one "episode". For example, in the top circle 10, the colour zones are the progressive positions of one wavefront as it passes over that region in the first such episode. It so happens that the wavefront in the next episode, depicted in the circle 12 below, also passes in the same direction and therefore its colour time map is similar. The third episode, however, (third small circle 14) is composed of a wavefront that arrives from a different direction (bottom right) and travels towards the top of the circular region, and therefore has a different arrangement of colours on the time map. In this example, the fourth episode, shown in circle 16 happens to be a non-uniform activation sequence in which wavefronts arrive from different directions and become extinguished in the central region of the circle. The fifth episode 18 is similar to the first two. This technique is well established and described in Kanagaratnam et al.

After a series of waves have been mapped, the operator can identify the episodes and form a view as to the predominant direction of propagation of wavefronts in each region, having set aside the wavefronts that are non-uniform in direction. This process of first identifying uniform activation episodes, and then collating their most common activation direction, as shown schematically in FIG. 2, can be used to determine the preferential uniform activation direction. This can then be repeated at multiple locations around the atrial endocardium until a preferential uniform activation map is created for the entire chamber, as shown in FIG. 3. If this is were practicable, it might in principle reveal the source of the rotor.

However, this technique is not practical to use in real life, because each wave may take several minutes to map and validate. Producing a preferential uniform activation map of the entire chamber may need several hundred waves to be analysed, which might take hundreds of hours using the current state of the art. This is not realistic for human patients undergoing clinical procedures.

We have previously disclosed in WO 2008/135731 a method and apparatus for generating a model of a cardiac surface with a plurality of electrogram voltages visualised upon it that permits, for a range of regular arrhythmias, the ready perception by the observer of the progress of activation around the heart. In brief, a series of short recordings of electrical voltage are acquired, one after the other, from different positions in the heart. Each acquisition takes place by pressing a contact catheter against one part of the heart, and making simultaneous recordings of both the voltage time course at that point and of the surface ECG.

The surface ECG of the patient is a repeating pattern which in these arrhythmias is stereotyped between one beat and the next. Likewise the recording from any particular location on the heart is also repetitive. This repeating nature permits all the individual recordings to be time-aligned against the surface ECG recordings, to provide a display of electrogram voltages from multiple sites at corresponding time points in the cardiac cycle. WO2008/135731 describes how these multiple recordings could be processed automatically without human intervention and then displayed with no delay, to form a progressively more rich display as the procedure continues and more data is available, giving a pictorial representation which doctors in the electrophysiology lab can interpret easily during the procedure to guide therapy in real time.

However, the irregular category of arrhythmias: those that do not show an obviously regular repetitive pattern in the surface ECG, are harder to characterise. The paradigm case of such an arrhythmia is atrial fibrillation. The method of WO 2008/135731 is not applicable to this category of arrhythmias because the fundamental requirement of a regular surface ECG is violated, and therefore synchronization cannot be achieved.

It is taught in Kanagaratnam et al that multi-electrode mapping is possible in chronic atrial fibrillation but it is time consuming and reveals a mixture of uniform and non-uniform activation. It has been taught in Narayan et al (Narayan S M, Krummen D E, Shivkumar K, Clopton P, Rappel W, Miller J M, MDTreatment of Atrial Fibrillation by the Ablation of Localized Sources CONFIRM (Conventional Ablation for Atrial Fibrillation With or Without Focal Impulse and Rotor Modulation) Trial. J Am Coll Cardiol 2012; 60:628-36) that it is possible to ablate at particular locations based on a circular pattern of motion of wavefront. The underlying process in atrial fibrillation is in many cases a "rotor", namely a sequence of electrical activation that is not composed of a single ring of activation, but a spiral arm in which activation spreads along a broad front, changing direction continually. The method proposed by Narayan et al to detect this pattern of activation is a series of contact electrodes placed in the atrium simultaneously, thus removing the requirement for a repetitive signal for synchronization of multiple short recordings. Narayan et al achieves this end by recording from all sites simultaneously.

One disadvantage of the Narayan approach is the requirement for complex, expensive, non-reusable equipment to be consumed for each patient that has no other application. Moreover, it does not allow intensification of focus in areas of special interest due to insufficient resolution.

A second disadvantage of the Narayan method is that it replaces the raw signals with a synthetic signal which is based on a standard fixed template of an idealised activation signal, distorted in the temporal direction in accordance with the local interval between supposed activations. The user sees on the screen the time courses of these synthetic signals (rather than direct observations from the patient). This is disadvantageous because in reality the voltage pattern of activation may vary significantly from site to site in the heart, and may also vary significantly between time to time. The automatic process of determining the onset of each activation episode is fallible, and when it misdetects the timing, such an error is forced to propagate throughout all future levels of processing. The reason for this that the Narayan method replaces the raw signal with the synthetic template-based signal, after which the user and indeed the later automatic processing has now been fed incorrect information but with no easy means to recognise that this information is incorrect. The user would have to attempt to recognise the error from the inconsistency from one site to another in activation timings, which is a difficult high-level skill and may be impossible especially in difficult clinical cases. More importantly, any automated process operating on such synthetic signals is severely handicapped because important information regarding reliability of activation time has been deleted and replaced with falsely-convincing synthetic data.

SUMMARY OF THE INVENTION

The present invention provides apparatus for monitoring activation in a heart, the apparatus comprising a probe, a plurality of electrodes supported on the probe and each arranged to detect electrical potential, for example at a respective position in the heart during a series of activations, and processing means arranged to analyse the detected electrical potentials, for example to identify a propagation direction of the activation, and optionally to generate an output indicative of that direction. The direction may be the only direction of propagation detected, or it may one of two or more detected directions. For example it may be a predominant direction of propagation.

The processing means may be arranged to analyse the detected potentials to determine at least one further parameter of the activation. The output may be dependent on the further parameter. For example the at least one further parameter may include the consistency of the direction of propagation of the activation. The consistency may be measured, for example by calculating a variance, or some other measure of variability, of the direction. The variance or variability may be over time, or over position, for example over the electrode sites.

The at least one further parameter may include a further direction of propagation of activation. For example this may be a subsidiary direction of propagation.

The apparatus may further comprise display means. The processing means may be arranged to control the display means to generate a display indicative of the direction or directions.

The processing means may be arranged to analyse detected potentials for a plurality of positions of the probe in the heart. The processing means may be arranged to control the display means to indicate simultaneously the direction of propagation at each of the positions of the probe.

The display means may be arranged to display a representation of the heart and to indicate the direction of propagation of the activation at a position, or positions, on the representation corresponding to the position, or positions, of the probe in the heart.

The control means may be arranged to control the display means to display a representation of the probe. The control means may be arranged to control the display means to indicate the direction of propagation relative to the probe, for example on the representation of the probe.

The apparatus may further comprise an imaging system, such as an X-ray system, arranged to display an image of the heart and the probe.

The display means may be arranged to indicate the direction of propagation by displaying a plurality of image objects moving in a corresponding direction on the display. The image objects may be dots, which may be round or square or of any other shape. The objects may have one or more parameters, such as size, colour, intensity or shape, which may be selected dependent on a parameter of the activation, such as the consistency of the direction of propagation. It is an advantage of this method of display that two or more directions of propagation can be shown at the same time in the same area. Alternatively the direction of propagation may be indicated by means of arrows or other suitable indicators.

The probe may comprise a lattice support structure, a plurality of electrodes supported on the lattice structure, a shaft connected to a first point on the lattice structure, and a control member connected to a second point on the lattice structure and movable relative to the shaft so as to vary the shape of the lattice structure.

Indeed the present invention further provides a probe for detecting electrical potentials at a plurality of positions in a heart, the probe comprising a lattice support structure, a plurality of electrodes supported on the lattice structure. The probe may further comprise a shaft connected to a first point on the lattice structure, and may also comprise a control member connected to a second point on the lattice structure. The control member may be movable relative to the shaft so as to vary the shape of the lattice structure.

The probe may further comprise a sheath. The shaft and lattice structure may be movable into the sheath so that the lattice structure can be inserted into the heart. The shaft and lattice structure may be movable out of the sheath so that that the lattice structure can be placed in contact with the heart.

The lattice structure may be hollow. The control member may extend through the lattice structure. The first and second points may be on opposite sides of the lattice structure.

The control member may be arranged to change the shape of the lattice structure between a plurality of different shapes or conditions. One shape may be a substantially flat operational shape or condition. One shape may be an elongate storage shape or condition.

In the flat operational condition, the lattice may have a front surface, and it may have a rear surface, and it may have a periphery. Each of these, if present, may have some of the electrodes on it.

The lattice structure may be formed of a plurality of filaments.

The present invention further provides apparatus for monitoring activation in a heart, the apparatus comprising a probe, a plurality of electrodes supported on the probe and each arranged to detect electrical potential at a respective position in the heart during an activation, and processing means arranged to process the detected electrical potentials and control the display means to display an image showing variation in the potentials with time during an activation event. The processing means may also be arranged to control the display means to display a direction indicator arranged to indicate a direction of propagation of the activation event, at the position of the probe, relative to the probe, wherein the direction of the direction indicator is adjustable in response to a user input.

The processing means may also be arranged to determine the position of the probe relative to the heart, and to determine therefrom the direction of the propagation, at the position of the probe, relative to the heart.

The display means may be arranged to display an image of the heart, and to display a further direction indicator arranged to indicate the direction of propagation relative to the heart.

The processing means may be arranged to determine the direction of propagation relative to the heart for each of a series or sample periods, and to display simultaneously a direction indicator for each direction of propagation. The display means may be arranged to display the direction indicators at respective positions on the image of the heart corresponding to the position of the probe on the heart during the relevant sample period.

By addressing specifically episodes of uniform activation, and ignoring the episodes of non-uniform activation, it may be possible to reconstruct the origin of a rotor. This can remove the difficulty of interpreting disorganised activation.

Some embodiments of the invention may provide an apparatus and method for preserving the temporal and amplitude detail of the raw electrogram data, and yet going beyond uniform activation to develop maps for use in the therapy of irregular activation such as fibrillation.

The method may analyse simultaneously parallel streams of data from multiple electrodes, which conveniently may all be mounted on a single multi-electrode catheter (many designs of which are known to those skilled in the art), to visualise activation direction in real time during the procedure.

The processing means may be arranged to determine the direction of propagation relative to the heart for each of a series of sample periods. The processing means may be arranged to control the display means to show the distribution of the directions of propagation. The processing means may be arranged to determine the direction of propagation for each sample period at each of a plurality of positions. The display means may be arranged to display a distribution at each of a plurality of respective positions on the image.

The processing means may be arranged to determine from the detected potentials interpolated values of at least one parameter of the detected potentials at positions having a spatial resolution which is finer than the spatial resolution of the electrodes. The processing means may be arranged to determine a direction of propagation at each of said positions. The positions may be on a regular grid.

Some attributes of preferred embodiments of the invention are that they do not require the observer to individually assign activation times at each location for each wavefront from the individual electrogram traces, nor do they replace raw data with synthetic templates constructed to look like idealised electrograms. Instead, the observer can, with some embodiments, determine visually without prior manual processing whether activation is uniform and at the same time assess the direction of activation. This process can be automated. At the same time, the 3D location of the electrodes can be available by any of several methods known to those skilled in the art. Combining the predominant direction of propagation of activation, with spatial location of the electrodes, permits automatic development of a map of movement of activation, with preferential emphasis given to uniform (more informative) activation over non-uniform (less informative) activation sequences, even when uniform and non-uniform activation episodes are intermingled in rapid succession.

The system may further comprise any one or more features, in any combination, of the embodiments of the invention which will now be described by way of example only with reference to the accompanying drawings.

Figure 4:
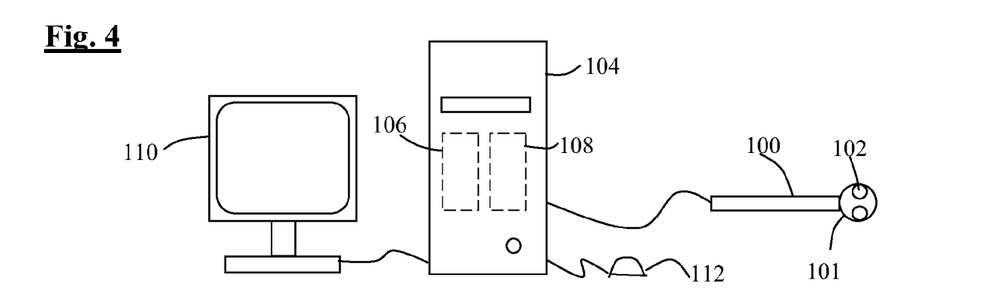
FIG. 4 is a diagram of a system according to an embodiment of the invention.

Referring to FIG. 4, a cardiac monitoring system according to an embodiment of the invention comprises a catheter 100 having a probe 101 at one end with a set of electrodes 102 located on it. Each of the electrodes 102 is connected independently through the probe catheter 100 to a computer 104 which is arranged to acquire, store and analyse the voltages detected by the electrodes 102. Specifically the computer 104 comprises a memory 106 and a processor 108. The processor is arranged to sample the voltages detected by the electrodes 102 at a regular sample rate and store the values of the sampled voltages in the memory 106, and then to analyse the stored voltage values so as to analyse the activation of the heart in the area contacted by the probe 101. Specifically the data can be analysed to identify focal targets within areas of irregular activation. The processor 108 is arranged to generate from the sampled voltage data, an image data set which it then provides to the display screen 110 which displays an image showing the activation pattern in the heart so that a user can interpret it. The probe 101 can be moved from region to region within the heart to focus attention in the regions where the targets are suspected.

The catheter 100 can be of any suitable design, many of which are commercially available catheters.

The data acquisition, data processing, and image display will now be described in more detail. The processor is arranged to perform each of these steps. For any particular position of the catheter 100, a stream of raw signal data is acquired from each of the numerous electrodes 102 of the catheter. The position of each electrode 102 is known through one of a variety of methods well known to those skilled in the art, such as those marketed as CARTO™ or NavX™. The following steps are then carried out by the system under the control of the processor 108. They are described here in sequence but they can occur almost simultaneously so that the operator sees the activation pattern at any position of the catheter 100 after only a minimal delay, for example less than a second.

In Step 1 the electrical data is acquired. Advantageously in Step 1 the catheter 100 and computer 104 are arranged to acquire unipolar electrogram data. A standard definition of unipolar electrogram data for a particular site is the potential difference between an intracardiac electrode at that site and a reference potential, for example at Wilson's central terminal, or any other combination of skin surface electrodes. Alternatively, a unipolar electrogram can be defined as the potential difference recorded between an intracardiac electrode and an electrode placed within the body at a site outside the heart, for example in the inferior vena cava, a large vein adjacent to the heart in which an electrode can very conveniently be located. Therefore a further electrode, not shown, is also provided and connected to the computer to provide the reference signal in known manner.

Less advantageously, bipolar electrogram data can be used, being defined as the potential difference between two intracardiac electrodes. The disadvantage of bipolar electrogram data is that it necessarily contains information from two sites, intermingled, which has two undesirable consequences. First, when a deflection in voltage (for example, positive) arises on a bipolar electrogram, it is not possible to know automatically whether this is caused by a rise in voltage at one site or a fall in voltage at the other site. Second, if a wavefront travels on the surface of the heart in a direction perpendicular to the line joining the two site, they will be activated essentially simultaneously, producing very similar voltage disturbances at the two electrodes such that the net difference between them, which is the bipolar electrogram, may register almost no disturbance despite the very clear event occurring.

Whether unipolar or bipolar electrogram signals are used, the signal from each electrode (or electrode pair) is sampled at a regular sample frequency and the sampled values stored in memory for analysis.

In Step 2, the electrogram data obtained in Step 1 is processed to enhance the features relating to local activation and de-emphasise the features relating to distant activation. Due to the irregular nature of atrial fibrillation and the relatively small amplitude of the signal that is desired to be enhanced, this is an imperfect process and the existence of this step will not result in a perfectly clear signal of local activation.

Step 2 consists of one or more of a family of processes broadly described as filtering. In this step, the morphology of the electrograms is altered substantially. A variety of filtering algorithms are well known to those skilled in the art. It is possible to apply one or more in sequence, using software programs coded operating on the microcomputer system 104 as in this embodiment. In other embodiments the processing is performed by hardware circuitry specifically designed or customised for filtering, known as digital signal processing hardware. A series of considerations are taken into account in selecting the algorithms applied in step 2.

Some filters have a feature of latency or delay. This is because their algorithm requires that they combine information from a long sequence of data elements to obtain the result for any time point. As an example, one possible filtering algorithm would be to take the arithmetic mean of the last 100 milliseconds of input data (ending at the current instant in time) to be the value of the output at the current instant in time. The effect of this is to introduce a delay of approximately 50 milliseconds into the data because when processing an input that is composed of infinitely long sequence of zero values with a single "one" value at time T, the output would be zero until time T, and then rise suddenly to a value of T/N (where N is the number of samples occurring within 100 milliseconds), and then remain at that level for 100 ms, before falling back down to zero. The net effect is an elevation in output during the time from 0 to 100 ms, whose centre time is 50 ms. An additional effect is that until 100 ms of input is available, valid output is not available. It is desirable that the filters in this disclosure do not introduce a long delay. This is achieved by ensuring that they do not require a long period of data before they can begin to produce output.

In this embodiment, Step 2 consists of three parts as shown in FIGS. 5a to 5d.

Figures 5A, 5B:
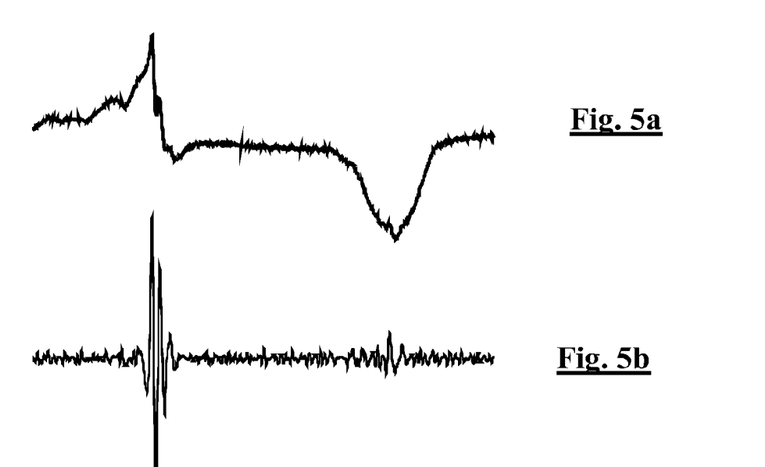
FIGS. 5a, 5b, 5c and 5d are time plots of signals from an electrode in the system of FIG. 4 after various different processing steps.

FIG. 5a shows the raw data from one electrode with unipolar voltage on the vertical axis and time on the horizontal axis. In Step 2a, generally undesirable features of the signal are removed, resulting in a signal as shown in FIG. 5b. In particular the large, low frequency components of the signal, and high frequency 'noise' are removed. This is commonly achieved with a bandpass filter, of which there are many designs known to those skilled in the art, and which preserves signals whose frequency is within a band of frequencies, while de-emphasising frequencies higher or lower than that band. For a unipolar electrogram, it is convenient for the bandpass filter to pass frequencies of 0.5-500 Hz. For a bipolar electrogram, while conventional frequencies are 30-500 Hz we have found it advantageous, considering the subsequent processing described in the following steps, to use a bandpass filter of 100-2000 Hz.

Figure 5C:
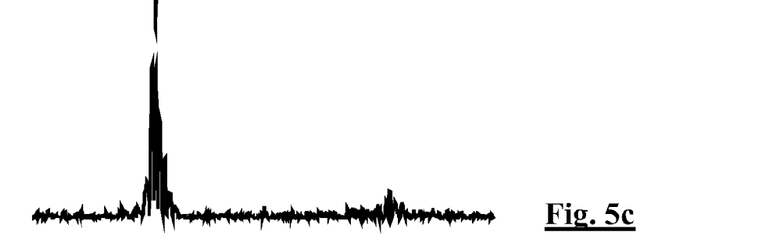

In Step 2b, the signal is converted into a purely positive signal by converting all negative values into corresponding positive values, a process known as rectification, to produce the result shown in FIG. 5c. In this embodiment this is done with the absolute value function, y=abs(x). In an alternative embodiment, this is achieved with the square function, y=x×x.

In Step 2c, the signal undergoes a further stage of filtering, which is low-pass filtering. This type of filtering is designed to blur the boundaries between the individual upward spikes during one activation sequence produced in 5c, so that the temporal region of activation is very distinct from the temporal region of no activation. This produces a smoothed trace, as exemplified in FIG. 5d. A variety of such filters are possible. In some embodiments this is achieved using a moving average filter. In this embodiment, this is achieved using convolution with a pattern that has a progressive rise and fall, such as the Hanning window function with duration conveniently chosen to be approximately the duration of an activation sequence. In an alternative embodiment, this is achieved using a Laguerre function. After each of these steps has been completed, the result is a set of data for each electrode recording values of the filtered and rectified electrical potential signal at a set of time points, and how it changes as a function of time. Each of these data sets defines a rectified and filtered signal for the respective electrode, and these signals can be displayed and analysed in various ways as will now be described.

Figure 5D:
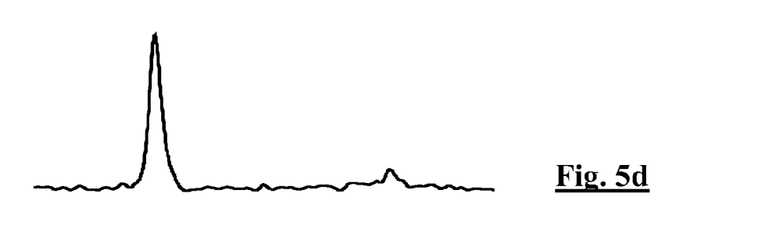

In Step 3 the signals produced by Step 2c, and shown in FIG. 5d, are displayed on the display 110 to allow the operator to instantly appreciate the progression of activation across that region of heart. This may vary between one episode and the next. The operator will be able to appreciate which is the predominant direction of progression. The catheter can then be moved to a new location, and again within a few seconds a new pattern of progression observed, and the new direction determined by the operator. By moving the catheter around the heart chamber in this manner, the operator can determine the predominant direction taken by the wavefronts across a region of heart chamber which is much larger than the size of the multi-electrode catheter itself. The display can be provided in a number of different ways, which in this embodiment are available as different display modes.

Figure 6:
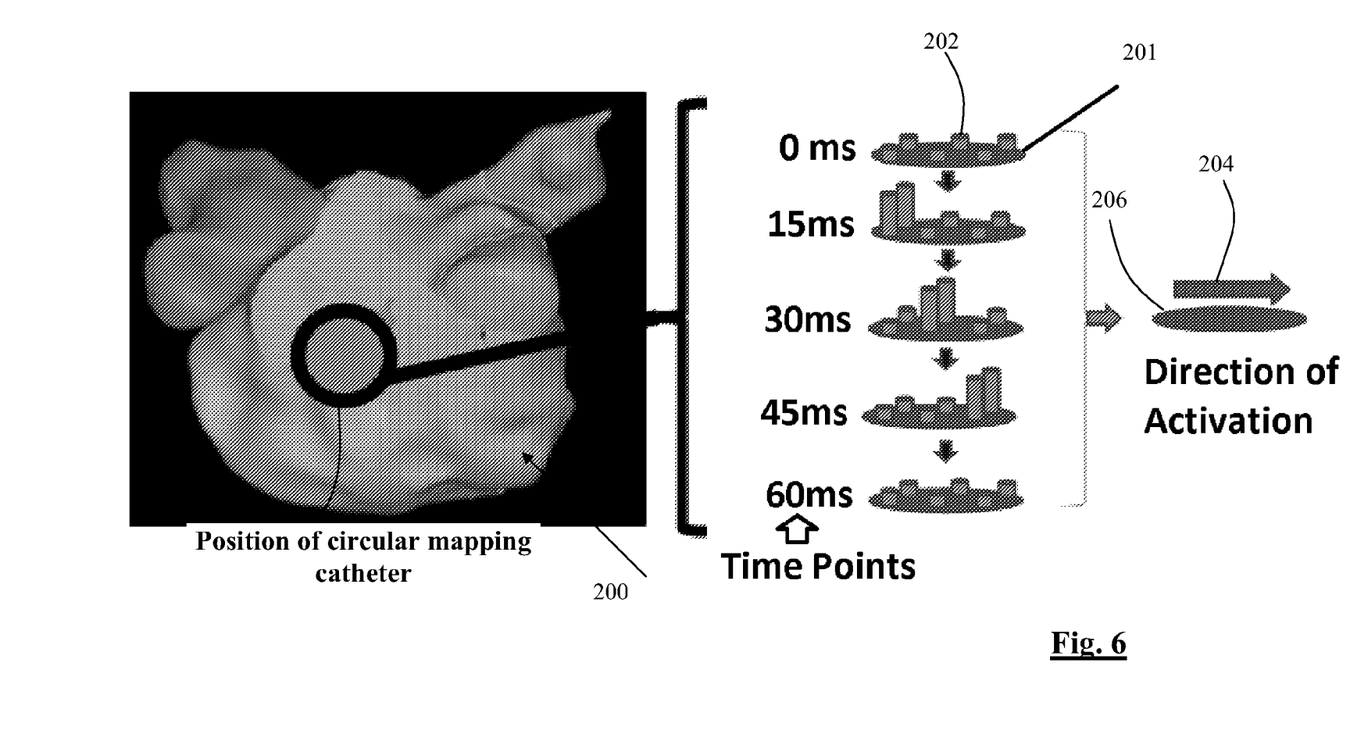
FIG. 6 is a schematic representation of a display generated on the system of FIG. 4.

Referring to FIG. 6, in the simplest display mode, the variations over time in the signals from the electrodes on the catheter are simply indicated for each position of the probe in the heart, and the operator retains this information mentally using no further system support. In this mode the signal at each of the electrodes 102 from the catheter are displayed at a 3D co-ordinate on a 3D representation 201 of the catheter corresponding to their actual position on the catheter 100. The voltage at each electrode 102 is displayed simultaneously as a dynamic bar 202 the length of which varies with time as the voltage varies. The numerical value of the voltage can undergo a logarithmic conversion to enable small signals to be seen as clearly as large signals. This allows the user to see uniform activation wavefront as the bars will move sequentially across the 3D representation. FIG. 6 shows how the display might vary over a set of 15 ms time intervals as an activation wave moves past the probe 101. In fact, as shown in FIG. 6, the representation of the probe is essentially flat and two-dimensional which is sufficient if the probe is arranged to contact only a relatively small area of the heart. This allows the lengths of the bars indicating the voltages to be compared easily as their bases are coplanar. The images showing the (filtered) instantaneous voltages at each of the electrodes at different times in the 60 ms sample period may be displayed on the display 110 simultaneously as shown in FIG. 6. Alternatively the bar lengths may be varied dynamically on the display over a display period to show the variation in voltage over the sample period. In this case the display period may be longer than the sample period so that the speed of the variation is slowed down on the display, so as to make the direction of propagation easier to determine.

Still referring to FIG. 6 and FIG. 1, in a further embodiment the computer 104 further comprises a user input, which could be a touch screen, but in this case is in the form of a mouse 112, arranged to allow a user to generate an input to the processor 108. The processor 108 is arranged to control the display 110 to display, as well as the images of the probe area 201 and bars 202 described above, an arrow or other direction indictor 204, the direction of which can be selected by a user via the user input 112. The direction indicator 204 is arranged to indicate a direction relative to the image of the probe 201. In this case this is achieved by displaying the arrow 204 next to a further image 206 of the probe 101. However the arrow can be shown, for example, under the image 201 of the probe on which the bars 202 are displayed. In either case, the direction of the arrow 204 is arranged to be varied in response to user inputs, so that the user can select manually the direction that it indicates relative to the image of the probe 201. The user inputs may be provided, for example, by a 'click and drag' operation of the mouse 112, or by touching the touch screen if one is provided. The processor 108 is then arranged to determine the position and orientation of the probe relative to the heart as described above, and from those data and the direction of the direction indicator 204 as selected by the user, determine the direction of progression of the activation relative to the heart at the position of the probe 201. The processor is arranged to display this direction, for example as an arrow, on the image 200 of the heart in a similar manner to that shown in FIG. 3, at a position on the image 200 of the heart corresponding to the position of the probe 101 on the heart. As the probe is moved around the heart, the direction of propagation at each position on the heart is recorded and displayed until a large enough area of the heart is covered.

Figure 2:
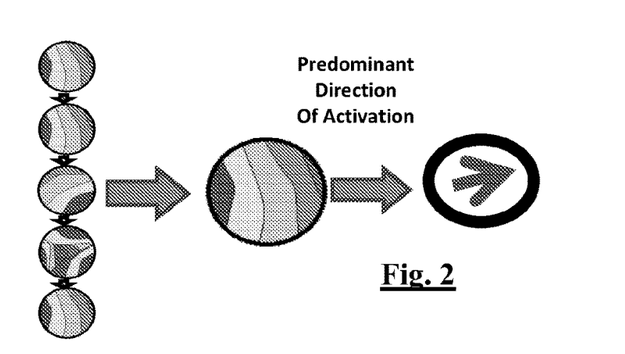
FIG. 2 shows schematically a further display on the known system of FIG. 1.
Figure 3:
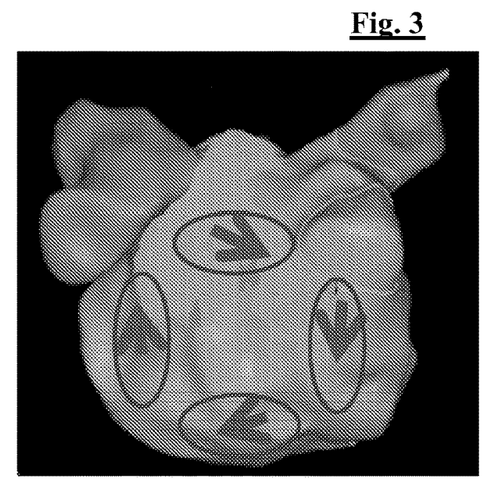
FIG. 3 shows a further image displayed on the system of FIG. 1.

Referring to FIGS. 1 and 2 in another embodiment, direction of motion is shown in the form of graduated coloration of the heart surface, as shown (in greyscale) in the right hand side of FIG. 1 and in FIG. 2. In this arrangement the area of the image is divided up into a series of separate areas with dividing lines between the areas extending perpendicular to the direction of travel of propagation. The colour graduations can be made to progress across the surface of heart in time. Conveniently these graduations could be a cyclic usage of a single colour map which progressed from a first colour gradually to a second colour and then gradually back to the first colour.

In another display mode, the direction of progress of the activation across the heart can determined by the processor, using a variety of techniques that will be described in more detail below, and displayed to the user, for example using an arrow to indicate the direction, for example as shown in FIG. 3. The step of acquiring the data is the same as described above with the probe 101 being moved to different areas of the heart and electrogram data acquired and stored for each area. Instead of (or as well as) being indicated directly using bars as described above, the processor is arranged for each position of the probe 101 to analyse the electrogram signals acquired over a period of time, and determine from them the direction of progression of the activation in that position. It will be appreciated that this can be done in many ways, for example identifying the positions of highest voltage at each point in time, constructing a line through them to represent the position of the wave peak, and then comparing the positions of the wave peak at subsequent points in time to determine the direction of movement. The direction for each probe position is then indicated on a representation of the heart as shown in FIG. 3 for each area of the heart that is contacted with the probe 101, using the known position of the probe.

In the example shown in FIG. 6, there is uniform activation across the circular catheter and the right-hand panel shows the direction of activation as represented by an arrow above the location of the circular catheter. After several locations are mapped using the circular catheter, it is possible to build up a 3D representation of the heart chamber of interest with the direction of preferential activation of uniform wavefronts at different locations within the chamber as shown in FIG. 3. Using the system of this embodiment, the preferential activation map similar to the conventional method can be achieved without the need to assign specific activation times to each electrogram within each time window. This technique is fast enough to be used in real time during cases unlike the conventional method.

The method of determining the direction progression of the activation described above will work if the activation is reasonably uniform. However in many cases it is not. Therefore in a more complex mode of operation the system is arranged to include further steps to assists in the determination of the predominant direction of wavefront progression. These steps include further computations which the computer is arranged to perform and which are arranged to analyse the electrogram data in more detail. First, the signals from each electrode, after being filtered as indicated in Step 2c, are summated into a single consensus signal expressing the commonality of behaviour over the entire multi-electrode array. The process for this is an arithmetic mean. In an alternative embodiment, the calculation of the mean is weighted by a value that describes the signal-to-noise characteristics of each site. This produces a single peak, in the consensus signal, for each episode of activation wavefront progression over this part of the heart. The time of the peak of this mean signal shall be referred to herein as $t_{Consensus}n$ for the "n"th activation wavefront. For the filtered electrogram data produced by Step 2c, from each individual electrode site, immediately before or after each of these $t_{Consensus}n$ times, there is a peak in the filtered electrogram. For example, if the process of the 15$^{th}$ activation involves a peak value at one site (let it be called s1) 5 milliseconds before the peak value at another site (s2), and 10 ms later a third site (s3) achieves peak value, and the consensus average waveform has a peak value at 7 ms after s1 which is denoted the $t_{Consensus}15$. Then, the time of peak at s1, denoted $t_{s1}15$, is −7 ms. Likewise $t_{s2}15$ is −2 ms and $t_{s3}15$ is +8 ms. Across all activations "n", the standard deviation, or other similar statistical measure of spread, of $t_{s1}n$ gives an indication of how stable is the timing of activation of site s1 within the set of sites. The variance, defined as the square of the standard deviation, is a another statistical measure which can be summed or averaged across sites to provide a single consolidated index covering all sites. In this example, the average stability of all sites can be given by the sum of the variances of $t_{s1}n$, of $t_{s2}n$ and of $t_{s3}n$. A high value of this sum of variances indicates poor consistency of the timings of activations in this region. A low value indicates high consistency.

In a further calculation step, the $t_{sj}n$ values, where j is the site number and n is the activation number, are considered a j×n matrix. (For avoidance of doubt the term $t_{sj}n$ represents the value of $t_{sj}$ at the n'th activation). Activations n1 and n2 that are similar to each other in direction of wavefront propagation will have similar values of $t_{sj}n1$ and $t_{sj}n2$ across all values of j, i.e. across all sites. The system is arranged to calculate the sum of squares term $$\Sigma^{(j=1 \text{ to number of sites})}(t_{sj}n1 - t_{sj}n2)^2$$

This sum is an index of how dissimilar the two activations n1 and n2 are to each other. In an alternative embodiment, the sum of the absolute differences is used:

$$\Sigma^{(j=1 \text{ to number of sites})}\text{abs}(t_{sj}n1 - t_{sj}n2).$$

Such formulas permit regions with homogeneous conduction to be identified automatically by the software, since they will have low values of this sum of discrepancies. Further, within any region, the activations can be grouped into two or more subgroups which minimise the within-group sum of squares, by one of many algorithms known to those skilled in the art. This "grouping of similar activations" permits regions that have two or more predominant directions of activation, to have those activation directions identified automatically.

As described above, in one display mode, the system is arranged to display graphically for the operator an image of the heart with an indication, at each site at which data has been acquired, of the degree to which the activations at that point are homogeneous versus inhomogeneous. This indication may be displayed on the surface of an image of a view of the 3 dimensional heart, coded by colour, brightness, transparency, stippling or cross-hatching. Alternatively, a number or other symbols could be written onto the surface. Alternatively a bar, line, or other structure can be drawn extending from the heart (or projecting into the chamber if the view is from the interior), whose size or other characteristic conveys this information. This allows the operator to rapidly identify homogeneous areas during the clinical procedure in real time.

In one mode, the system is arranged to automatically determine the direction of propagation in the region covered by the multipolar electrode using information on the 3-dimensional location of each site obtained by methods described above. From the set of relative timings of local activation calculated above as $t_{sj}n$, the direction of activation is estimated by assuming that there is a uniform conduction velocity in the region. A function where activation time T varies linearly with position is then fitted to the actual activation times. In two dimensions denoted x and y, in general the function would be T(x,y)=a x+b y, where the velocity in the x direction is a, and the velocity in the y direction is b. The overall velocity is then $(a^2+b^2)^{1/2}$. The values of a and b are chosen, by one of many methods well known to those skilled in the art, to minimise the discrepancy between T(x,y) and the actual measured activation times at each site on the catheter.

This process of choosing a and b to find a best fit activation timing function may occur separately for each activation wavefront (permitting direction to be independently stated for each activation). Alternatively the activations may be assembled into groups by the method described above as "grouping of similar activations". Within each group of similar activations, the direction of travel of the wavefront is relatively consistent, compared with the degree of consistency of all activations together. Thus a single T function, ie a single pair of values for a and b, is obtained for the entire group of similar activations, even if these activations are not sequential. For example, if the first, sixth and eighth activation are of grouped as similar, and the second, fifth and ninth are also grouped as similar, with the others not grouped, then there would be one T function for activations 1, 6, 8 and another for activations 2, 5, 9, and individual T functions for the other beats.

One method of finding the best fit timing function involves a 'least squares best fit' process of choosing a and b is to minimise the sum of the squared error across the cardiac sites (and across the activations if more than one is being considered), between T(x,y) and the actual activation times for that activation or group of similar activations.

Formally, for a single activation (number n), and with the j'th site on the catheter identified as $s_j$, at position $x_j$ and $y_j$, this process is to minimise the value of the following formula $\Sigma$(across all sites $s_j$)$(T(x_j,y_j)-t_{s_j}n)^2$.

In the case of a group of N similar activations (n1, n2, . . . , nN) each denoted $n_i$ with i taking values from 1 to N, this process is to minimise the value of the following formula $\Sigma$(across activations $n_i$ representing $n1, n2, \ldots, nN$)
(across all sites $s_j$)$(T(x_j,y_j)-t_{s_j}n_i)^2$.

A variety of alternative methods are available which select the values of a and b in the T formula by minimising some other function of $T(x_j,y_j)$ and $t_{s_j}n$, with similar results. For example, minimisation of the sum of the absolute difference is an alternative embodiment, in which case the above formulae become, respectively, $\Sigma$(across all sites $s_j$)$|T(x_j,y_j)-t_{s_j}n|$ and $\Sigma$(across activations $n_i$ representing $n1, n2, \ldots, nN$)
(across all sites $s_j$)$|T(x_j,y_j)-t_{s_j}n_i|$ From the fitted T function, the system is arranged to calculate the direction of activation by calculating the gradient of the T function. The closer the fit (the smaller the residual error component), the more reliable the direction calculation. On the display screen the computer is then arranged to display for that site on the heart, graphical information that conveys to the operator:
 the direction (or directions) of wavefront propagation at that site;
 the degree of homogeneity of conduction at that site;
 the degree of reliability of the direction calculation.

In one embodiment, this is in the form of one or more arrows. Properties of the arrow (such as colour, length, boldness, transparency, degree of elevation from the surface, nature of "head" and "tail" elements) may convey the information elements listed above.

Figure 8:
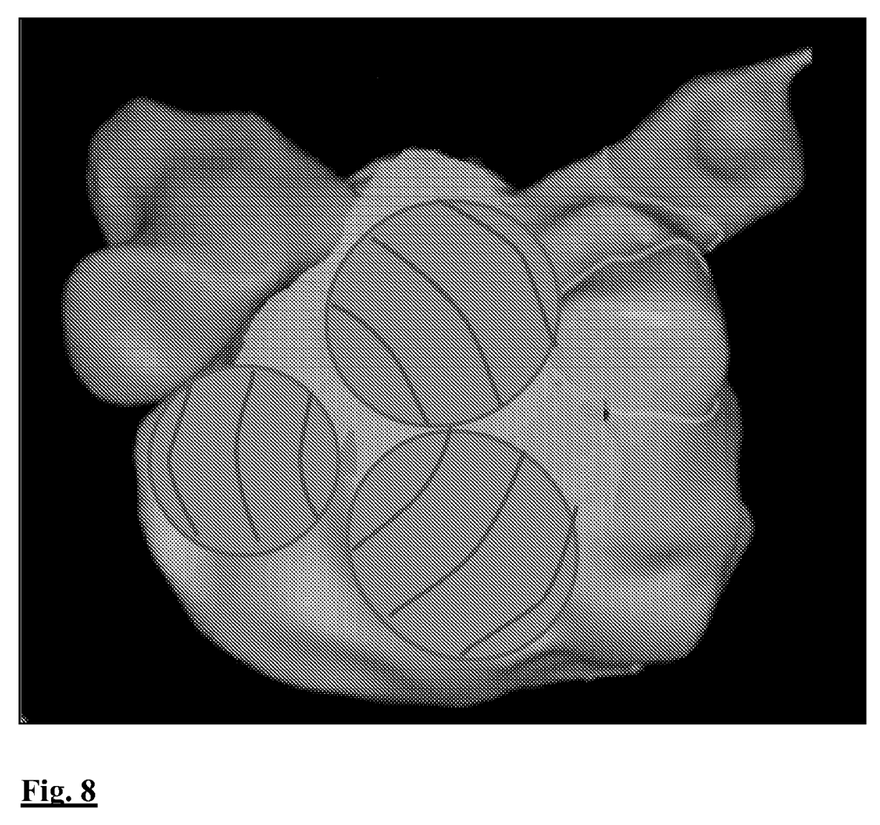
FIG. 8 shows an image displayed in a further embodiment of the invention.

Referring to FIG. 8 in another embodiment, direction of motion is shown in the form of a series of curves which, advantageously, may migrate progressively across the region of the heart. This depiction, whether static or moving, is readily perceived by a human operator as indicating direction of activation. Multiple activations can be displayed simultaneously and, advantageously, may be displayed in separate colours.

In another embodiment, direction of motion information is conveyed by a synthetic pattern of moving dots that travel across the surface of the heart in a pattern corresponding to the set of velocities identified in the steps above. By way of example, if after observing 20 activations it is seen that 50% of the activations are directly left-to-right, and 25% are top-to-bottom, and the remainder are a mixture, then a number of dots such as 20 could be created within a circular disc-shaped region representing the position of the catheter. Ten would be in a continuous left-to-right movement pattern, with the proviso that when they reached the right edge of the disc they would disappear and reappear at the left. Five would similarly move in a top-to-bottom direction. The remaining five would then move according to the patterns of the individual (non-grouped) activations observed at that point.

In this "moving dot" embodiment, dots which represent large groups and/or strong consistency within a group and/or a high degree of fit to the T function, may be advantageously displayed larger or in a more intense colour. Conversely dots which represent individual non-grouped (ie inhomogeneous) activations could be shown smaller and/or in a faint colour. In this embodiment, therefore, a pattern of regular activation such a sinus rhythm would manifest as bright, large dots moving in a consistent pattern all over the heart; in contrast, a pattern of totally irregular activation would manifest as small grey dots moving in an inconsistent pattern, criss-crossing each other, ever the whole heart. A pattern of a focal (or rotating) origin of arrhythmia surrounded by irregularity would manifest as a region of large bright dots moving in a roughly circular pattern in one area interspersed with occasional small dots moving in inconsistent directions. Progressively further away from the origin of the arrhythmia, there would be greater intrusion of the non-grouped dots, until at some distance away the non-grouped dots are the overwhelming majority. The operator can appreciate the pattern as it is assembled from acquisitions at different sites in the heart, in a manner akin to appreciating the pattern of a jigsaw from pieces if their correct location is known. This display method uses to advantage the highly evolved brain function of seeing patterns in moving dots even in the presence of some dots moving inconsistently.

During organized activation the direction of the wavefront can be determined by using multi-electrode mapping as described above if the 3D location of the electrodes and the activation time is known. FIG. 3 illustrates one example of how this can be represented on a 3D image of the chamber. The technique for targeting the focal/rotor source using this technique would be taught as a part of a training course in interpretation of these organised fibrillatory activation maps. In the most simple form as shown in FIG. 3 there is preferential organised fibrillatory activation in a circuit. In this case the centre of this circuit would be mapped and targeted for ablation.

In a further embodiment, instead of a realistic representation of the heart's surface as shown in FIG. 3, a standardised shape is displayed which approximately represents the geometry of the catheter, and the direction of propagation is displayed on that standardised shape in any of the ways described herein. This can be similar to the display shown in FIG. 6 in which the probe shape is shown as a simple disc, but where the probe shape is more complex it can be represented as a 3D shape. This permits activation to be mapped within the local area of the catheter without the apparatus requiring information the 3-dimensional localisation of the electrodes. In a system where the subject is imaged on an X-ray imaging system, and the catheter will therefore be displayed in an X-ray image of the subject, the human operator can interpret the display of the direction of propagation on the standardised image of the catheter in light of the appearance, and the position in the x-ray image, of the catheter.

Figure 9:
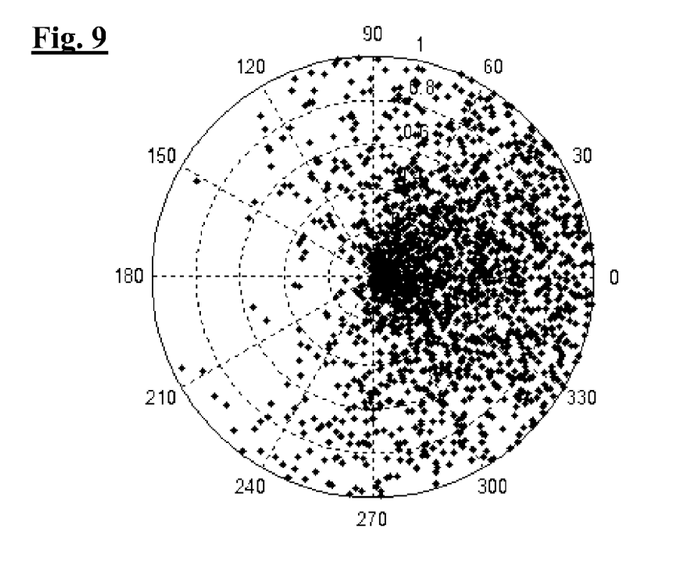
FIG. 9 is a plot of propagation direction data accumulated over time.
Figure 10:
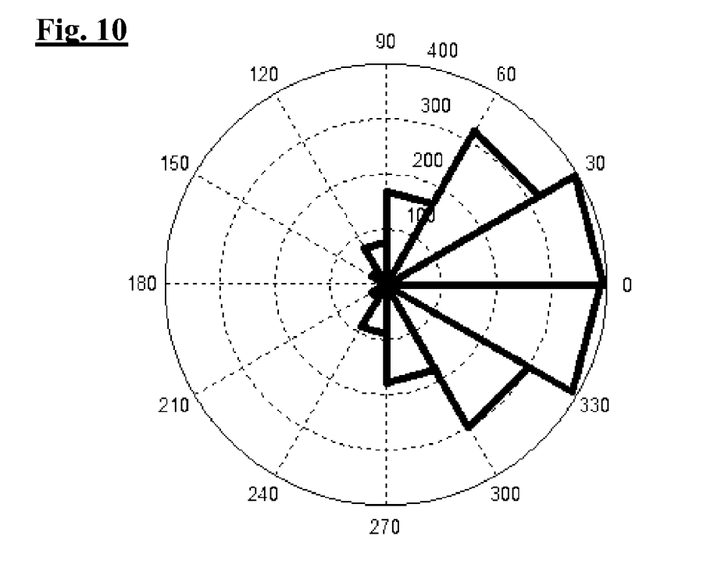
FIG. 10 is a polar histogram of the data of FIG. 9.
Figure 11:
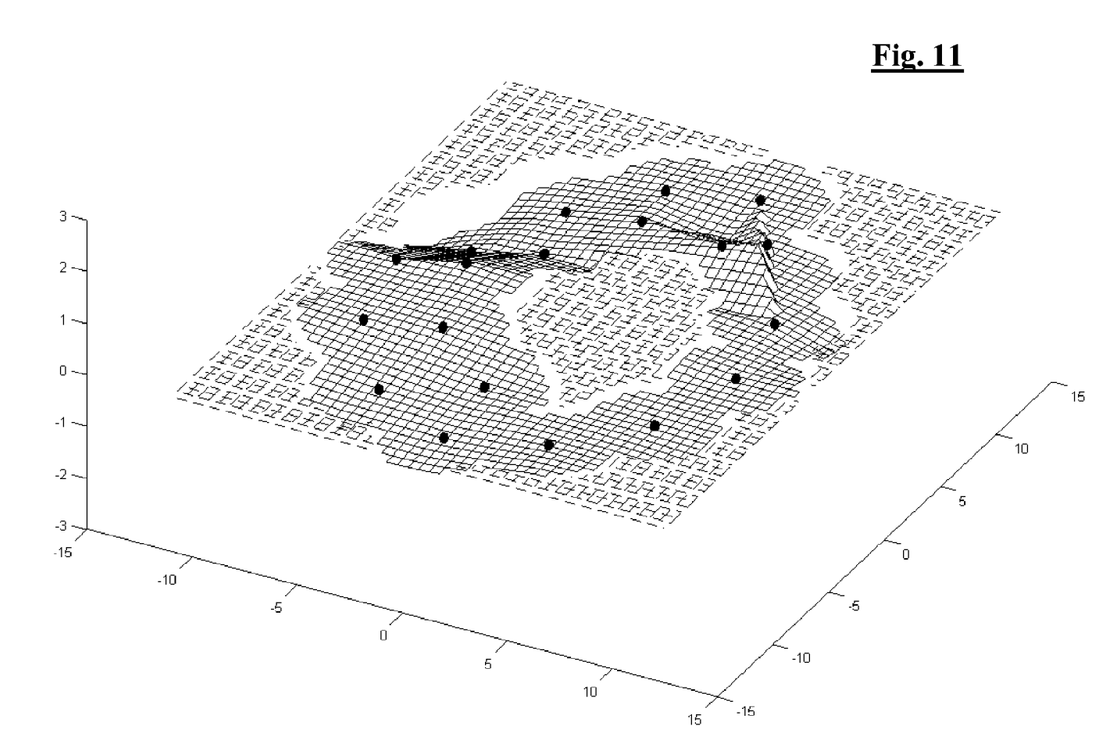
FIG. 11 is a 3D plot of interpolated electrode voltage data displayed in a further embodiment of the invention.

Referring to FIGS. 9 and 10 in a further embodiment the system is arranged determine the direction of propagation in one position, or a group of positions, on the heart at each of a series of sample periods. It is the arranged to store the determined directions as a set of propagation direction data, and analyse that data and generate a display based on the analysis. In the example shown in FIG. 9, a series of propagation samples are stored, each one having a direction of propagation and a strength (for example as determined from the amplitude of the electrode signal variation) associated with it. Each of these samples can be displayed on a polar plot as shown in FIG. 9, with the direction indicated as the direction from the origin and the strength as the distance from it. This data can also be displayed as a polar histogram or rose plot as shown in FIG. 10. Where the data relates to all, or several, positions on the heart, the plot can be displayed as a stand-alone display. Where the data relates to the propagation directions at one position, or a group of neighbouring positions, on the heart, the plot can be displayed superimposed on an image of the heart or part of the heart at a position to indicate the position in the heart to which the data relates. Several plots can be displayed at respective positions on the image of the heart, or part of the heart. Referring to FIG. 11 in a further embodiment, the system is arranged to calculate interpolated signal features on a finely spaced grid, conveniently a square grid with spacing 0.5 mm in each direction. The processor is arranged to achieved this by cubic spline interpolation of the signal features obtained at each electrode position across the heart surface, or across a flat two dimensional representation of the electrode positions in relation to each other. At each instant in time, therefore, there is an interpolated signal characteristic at each gridpoint on the regular grid. This data structure is plotted as a surface or as a wireframe mesh. The interpolated signal characteristic is used to set the colour of the mesh at that point or its notional elevation in the third dimension. Since a new set of interpolated values is calculated, and a mesh is drawn, for every instant in time (e.g. every signal sample period), the values for each sample period can be displayed in sequence such that the appearance gained by the observer is of a continuous movie, indicating the progression of wavefronts across the region being studied.

The signal characteristic being plotted can be the spatially interpolated voltage at that position at that instant in time, as shown in FIG. 10. Rather than the raw voltage, the characteristic may be the voltage after it has undergone a transformation to its absolute value, square root of absolute value, absolute value raised to a fixed power such as 0.5 or 2, or sign multiplied by the square of the absolute value (which resembles the square root transform but preserves the sign).

The rotor mapping methods described above can be performed using any suitable multi-electrode catheter. However, there are certain features of the catheter and probe which are particularly advantageous for rotor mapping and a suitable catheter according to one embodiment of the invention will now be described with reference to FIGS. 7a, 7b and 7c.

Figures 7A, 7B, 7C:
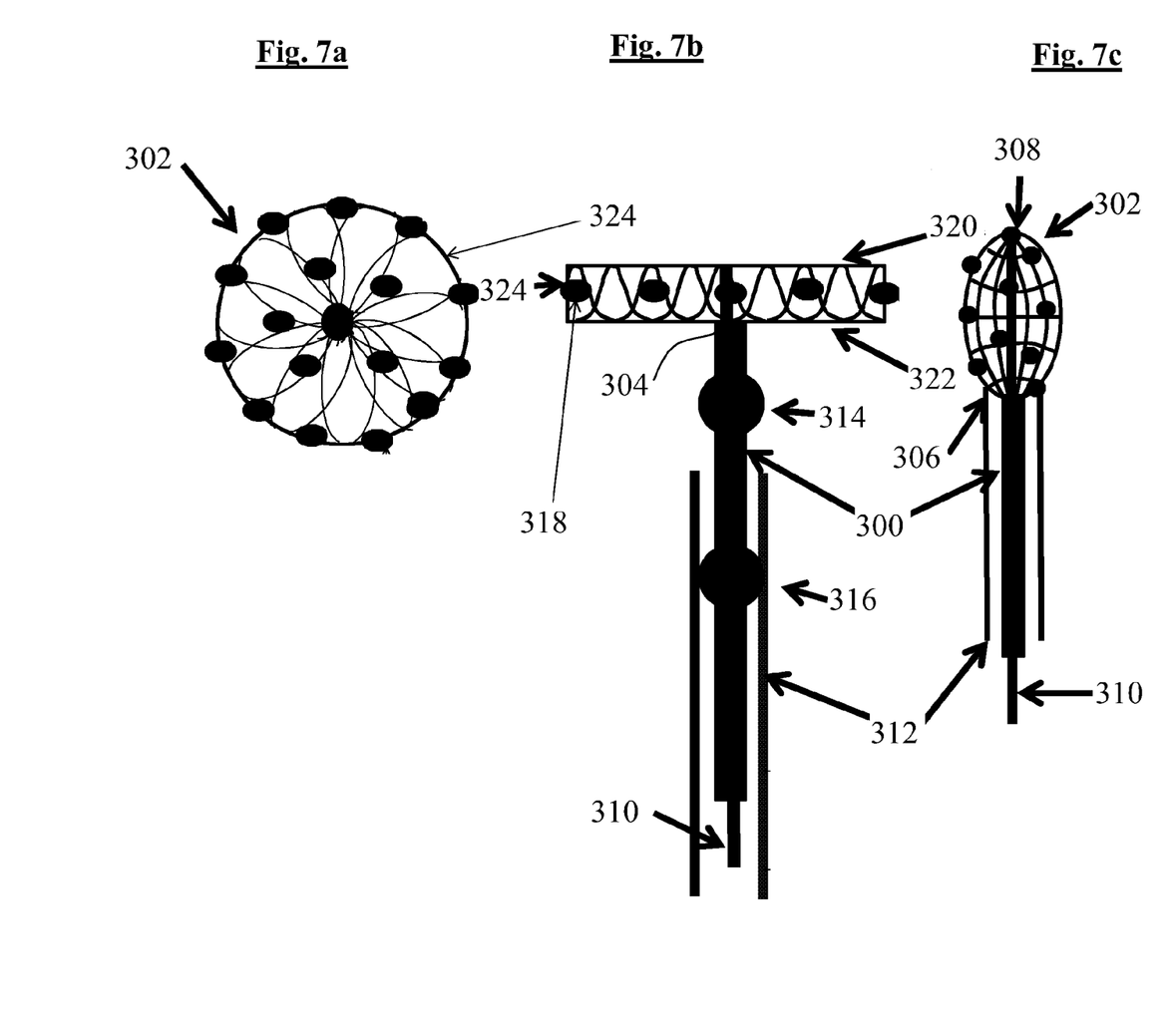
FIGS. 7a, 7b and 7c are different views of a probe forming part of the system of FIG. 4.

The catheter is constructed of a hollow shaft 300 with an expandable mapping lattice 302 mounted on its distal end 304. The lattice is formed of filaments or elements 303 and is deformable, but can form a substantially spherical surface as shown in FIG. 7c, with its inner end 306 and outer end 308 separated by an intermediate distance. The inner (proximal) end 306 is attached to the distal end of the shaft 300, which is hollow, and its outer (distal) end 308 attached to the distal end of an inner shaft 310 which extends through the hollow shaft 300 and through the interior of the lattice 302. The inner shaft 310 can be moved longitudinally through the hollow shaft 300 to vary the shape of the lattice 302 by means of handles on the ends of the shafts. The lattice 302 can be collapsed into a generally flat circular shape by pulling its outer end 308 towards its inner end 306 as shown in FIG. 7b, or extended into an elongate shape by pushing its outer end 308 away from its inner end 306 beyond the position shown in FIG. 7c. In the fully extended condition the electrodes and the lattice are flush with the sides of the inner shaft 310 and the lattice can be retracted into an outer sleeve 312 of the catheter. Electrodes 314, 316 are mounted on the hollow shaft 300 spaced from its distal end 304. The voltages from these electrodes are used to provide the reference voltage for the unipolar electrogram.

The flexible lattice probe is specifically designed to collect electrical data from the heart for the purposes of applying the algorithms for interpreting irregular activation patterns. In this embodiment the lattice 302 is made from nitinol, but other materials, such as other compressible or "memory" materials suitable for use within the heart can be used. The lattice may be disc shaped in the collapsed condition, or polygonal (such as square, pentagonal or hexagonal). In this state it can be pressed up against the cardiac wall. Due to its compressible nature will not cause injury to the cardiac wall. Electrodes 318 are supported on the lattice 302 and placed in such a manner around the lattice on its front surface 320 that faces away from the catheter sleeve 312, its rear surface 322 which faces back towards the sleeve 312, and its peripheral surface 324 which faces radially outwards. The electrode array enables electrogram data to be collected from the cardiac wall, regardless of which surfaces of the lattice are touching the wall. Each of the electrodes is electrically connected to a respective connector that extends through the hollow shaft 300 so that the electrical potential at each of the electrodes can be detected and input to the computer 104 for analysis as described above.

The lattice can be pushed up against the heart wall to record from its front surface 320 or into the pulmonary veins/superior vena cava/coronary sinus to record from its outer surface 324 or pulled back against the septum to record from its rear surface 322. The electrodes 318 are positioned so that when the lattice is stretched out in its fully extended position it can be safely inserted into an outer sheath 312 without damaging the electrodes 318, lattice 302 or sheath 312.

The catheter is arranged to be supplied pre-packaged in its linear, stretched conformation with the lattice 302 stretched out so that it can fit within the sheath 312 which is passed into the heart by standard methods well known to those skilled in the art. When the outer catheter 312 is in position in the left atrium the lattice probe 302 is pushed out of the sheath 312 and the inner shaft 310 is pulled to move the distal end 308 and proximal end 306 closer together which extends and opens the elements or splines of the lattice 302 outwards to form the collapsed discoid conformation. This causes the slender individual lattice elements 303 of the mapping lattice 302 to open out into an extended conformation as shown in the end-face view in FIG. 7a and side view in FIG. 7b. The mapping lattice 302 has electrodes on both front 320 and back 322 faces and also on the outer periphery 324.

The catheter is steerable, for example using pull wires in the inner or outer shafts 310, 300 or in the sheath 312 controlled by a mechanism in the handle of the shaft or the sheath. The clinician uses this steering system, as well as pulling and pushing, and manipulation of the outer catheter, to move the lattice probe 302 into contact with the internal wall of the heart as is well known by those expert in field. By gently increasing the pressure applied by the catheter on the internal wall of the heart, the shape of the mapping lattice is made to conform more closely to the shape of the wall, so that there is efficient contact across the contact surface. To move the catheter to a new position, the operator withdraws it slightly to bring it off contact with the wall, and then spins or deflects the tip to another location, or redirects the sheath taking the catheter with it. In each position, the computer 104 controls the display 110 to show the operator visually the patterns of activation locally in an easily interpretable manner as described above. By steps such as these, the walls of the atrium can be mapped, with the ability to give special attention to areas which are showing patterns suggesting the origin of pathological rhythms. The catheter is removed from the patient by first pulling the hollow shaft 300, which causes the mapping lattice 302 to return into its linear conformation, and then withdrawing it through the outer sheath 312.

The catheter described above has various specific features which are desirable for rotor mapping. These include a high density of electrodes on a soft compressible lattice lobe which enables high resolution mapping, and the fact that all surfaces have electrodes to enable data collection from any orientation.

The invention claimed is:

1. Apparatus for monitoring activation in a heart, the apparatus comprising a probe, a plurality of electrodes arranged in an array and supported on the probe and each configured, for a position of the probe, to detect electrical potential at a respective position in the heart during a series of activations of the heart, and a processor configured to analyse the detected electrical potentials to identify a respective propagation direction of each of the series of activations at each of the positions, and, for each of the positions, to generate a first output indicative of the direction of at least one of the activations, for each of the positions, determine a consistency of the propagation directions over the series of activations, and for each of the positions, generate a second output indicative of the consistency of the propagation directions.

2. Apparatus according to claim 1 wherein said direction is a first direction and second output is indicative of a second direction of propagation of activation of at least one of the activations, and the second direction is different from the first direction.

3. Apparatus according to claim 1 further comprising a display screen wherein the processor is configured to control the display screen to generate a display indicative of the direction and the consistency of the directions.

4. Apparatus according to claim 3 wherein the processor is configured to analyse the detected potentials for a plurality of positions of the probe in the heart, and control the display screen to indicate simultaneously at least one direction of propagation at each of the positions of the probe.

5. Apparatus according to claim 3 wherein the processor is configured to control the display screen to display a representation of the heart and to indicate the direction of propagation of the activation at a position on the representation corresponding to the position of the probe in the heart.

6. Apparatus according to claim 3 wherein the processor is configured to control the display screen to display a representation of the probe and to indicate the direction of propagation relative to the probe, on the representation of the probe, the apparatus further comprising an imaging system configured to display an image of the heart and the probe.

7. Apparatus according to claim 3 wherein the processor is configured to control the display screen to indicate the direction of propagation by displaying a plurality of image objects moving in a corresponding direction on the display.

8. Apparatus according to claim 1 further comprising a display screen, wherein the processor is configured to determine the direction of propagation relative to the heart, at at least one position, for each of a series of sample periods and to control the display screen to show the distribution of the directions of propagation at said at least one position.

9. Apparatus according to claim 1 wherein the processor is configured to determine from the detected potentials interpolated values of at least one parameter of the detected potentials at positions having a spatial resolution which is finer than a spatial resolution of the electrodes, and to determine a direction of propagation at each of said positions.

10. Apparatus for monitoring activation in a heart, the apparatus comprising a probe, a plurality of electrodes arranged in an array and supported on the probe and each configured to detect electrical potential at a respective position in the heart during a series of activations of the heart, a display screen, and a processor configured to process the detected electrical potentials and control the display screen to display an image showing variation in the potentials with time during each of the activation events, and also configured to control the display screen to display a direction indicator configured to indicate a direction of propagation of at least one of the activation events relative to the probe, wherein the processor is further configured to receive a user input and to adjust the direction of the direction indicator in response to the user input.

11. Apparatus according to claim 10 wherein the processor is also configured to determine the position of the probe relative to the heart, and to determine therefrom the direction of the propagation relative to the heart.

12. Apparatus according to claim 11 wherein the processor is configured to control the display screen to display an image of the heart, and to display a further direction indicator arranged to indicate the direction of propagation relative to the heart.

13. Apparatus according to claim 12 wherein the processor is configured to determine the direction of propagation relative to the heart for each of a series of sample periods, and to display simultaneously a direction indicator for each direction of propagation.

14. Apparatus according to claim 13 wherein the processor is configured to control the display screen to display the direction indicators at respective positions on the image of the heart corresponding to the position of the probe during the relevant sample period.

15. An apparatus for monitoring activation in a heart, comprising:
- a probe;
- a plurality of electrodes arranged in an array and supported on the probe and each electrode configured, for a position of the probe, to detect electrical potential at a respective position in the heart during a series of activations of the heart;
- a processor with memory; the memory comprising non-transitory instructions that when executed by the processor:
  - analyse the detected electrical potentials to identify a respective propagation direction of each of the series of activations at each of the positions;
  - generate, for each of the positions, a first output indicative of the direction of at least one of the activations;
  - determine, for each of the positions, a consistency of the propagation directions over the series of activations; and
  - generate, for each of the positions, a second output indicative of the consistency of the directions.

* * * * *